US008709779B2

(12) United States Patent
Gonzalez et al.

(10) Patent No.: US 8,709,779 B2
(45) Date of Patent: Apr. 29, 2014

(54) NEWLY IDENTIFIED HUMAN RHINOVIRUS OF HRV-C AND METHODS AND KITS FOR DETECTING HRV-CS

(75) Inventors: Richard Gonzalez, Beijing (CN); Jianwei Wang, Beijing (CN); Zichun Xiang, Beijing (CN); Kunling Shen, Beijing (CN)

(73) Assignees: Biomerieux, Marcy l'Etoile (FR); Institute of Pathogen Biology, Chinese Academy of Medical Sciences, Beijing (CN); Beijing Children's Hospital Affiliated to Capital Medical University, Beijing (CN)

( * ) Notice: Subject to any disclaimer, the term of this patent is extended or adjusted under 35 U.S.C. 154(b) by 317 days.

(21) Appl. No.: 12/936,004

(22) PCT Filed: Apr. 16, 2009

(86) PCT No.: PCT/CN2009/071310
§ 371 (c)(1),
(2), (4) Date: Dec. 10, 2010

(87) PCT Pub. No.: WO2009/127154
PCT Pub. Date: Oct. 22, 2009

(65) Prior Publication Data
US 2011/0111391 A1  May 12, 2011

(30) Foreign Application Priority Data
Apr. 17, 2008 (WO) ............... PCT/CN2008/000785

(51) Int. Cl.
*C12Q 1/70* (2006.01)
*C12N 7/00* (2006.01)
*C07H 21/00* (2006.01)
*C12Q 1/68* (2006.01)
*C07K 14/095* (2006.01)
*G01N 33/569* (2006.01)
*C07K 7/08* (2006.01)
*C07K 16/10* (2006.01)

(52) U.S. Cl.
CPC .............. *C12N 7/00* (2013.01); *C12N 2770/00* (2013.01); *C12N 2770/00021* (2013.01); *C12N 2770/32711* (2013.01); *C12N 2770/32721* (2013.01); *C12N 2770/32011* (2013.01); *G01N 33/569* (2013.01); *G01N 33/56983* (2013.01)
USPC ........ 435/235.1; 435/5; 536/23.1; 536/24.33; 536/24.32; 530/350; 530/326; 530/389.4

(58) Field of Classification Search
CPC ............ A61K 39/12; A61K 2039/522; A61K 2039/525; A61K 2039/5252; A61K 2039/5258; A61K 2039/543; A61K 35/76; C12N 7/00; C12N 2760/14121; C12N 2770/32721; C12N 2770/36121; C12N 2770/32711; C12N 2770/32011; G01N 2333/918; G01N 2333/40; G01N 2800/60; G01N 33/56961; G01N 33/5767; G01N 33/569; G01N 33/571; G01N 33/576; C07K 14/005
USPC ........ 435/5, 6, 235.1; 536/23.1, 24.33, 24.32; 530/350, 326, 389.4
See application file for complete search history.

(56) References Cited

U.S. PATENT DOCUMENTS

2009/0275636 A1* 11/2009 Briese et al. ................. 514/44 A
2010/0233677 A1*  9/2010 Liggett et al. ..................... 435/5
2012/0114661 A1*  5/2012 Ginsburg et al. ........... 424/147.1
2012/0122081 A1*  5/2012 Waris et al. ....................... 435/5

FOREIGN PATENT DOCUMENTS

JP      A-63-219384      9/1988
JP      A-2003-093057    4/2003

OTHER PUBLICATIONS

McErlean P, Shackelton LA, Lambert SB, Nissen MD, Sloots TP, Mackay IM. Characterisation of a newly identified human rhinovirus, HRV-QPM, discovered in infants with bronchiolitis. J Clin Virol. Jun. 2007;39(2):67-75. Epub May 7, 2007.*

Lamson D, Renwick N, Kapoor V, Liu Z, Palacios G, Ju J, Dean A, St George K, Briese T, Lipkin WI. MassTag polymerase-chain-reaction detection of respiratory pathogens, including a new rhinovirus genotype, that caused influenza-like illness in New York State during 2004-2005. J Infect Dis. Nov. 15, 2006;194(10):1398-402. Epub Oct 6, 2006.*

Kistler, A., Avila, P.C., Rouskin, S., Wang, D., Ward, T., Yagi. S., Schnurr, D., Ganem, D., DeRisi, J.L. and Boushey, H.A. (2007). Pan-viral screening of respiratory tract infections in adults with and without asthma reveals unexpected human coronavirus and human rhinovirus diversity. J. Infect. Dis. 196: 817-825. Epub Aug. 6, 2007.*

Lau, S.K., et al. (2007). Clinical features and complete genome characterization of a distinct human rhinovirus genetic cluster, probably representing a previously undetected HRV species, HRV-C, associated with acute respiratory illness in children. J. Clin. Microbiol. 45: 3655-3664.*

McErlean, P., Shackelton, L.A., Andrews, E., Webster, D.R., Lambert, S.B., Nissen, M.D., Sloots, T.P. And Mackay, I.M. (2008), Distinguishing molecular features and clinical characteristics of a putative new rhinovirus species, Human rhinovirus C (HRV C). PLoS One 3(4): e1847.*

Arden KE, McErlean P, Nissen MD, Sloots TP, Mackay IM. Frequent detection of human rhinoviruses, paramyxoviruses, coronaviruses, and bocavirus during acute respiratory tract infections. J Med Virol. Sep. 2006;78(9):1232-40.*

Beckman-Coulter. "Codon optimization to PCR." Nature. Oct. 2, 2003; vol. 425:540.*

Xiang Z, Gonzalez R, Xie Z, Xiao Y, Chen L, Li Y, Liu C, Hu Y, Yao Y, Qian S, Geng R, Vernet G, Paranhos-Baccalà G, Shen K, Jin Q, Wang J. Human rhinovirus group C infection in children with lower respiratory tract infection. Emerg Infect Dis. Oct. 2004;14(10):1665-7.*

Kistler et al., Pan-Viral Screening of Respiratory Tract Infections in Adults With and Without Asthma Reveals Unexpected Human Coronavirus and Human Rhinovirus Diversity, *The Journal of Infectious Diseases*, 2007, vol. 196.

(Continued)

*Primary Examiner* — Benjamin P Blumel
*Assistant Examiner* — Rachel Gill
(74) *Attorney, Agent, or Firm* — Oliff PLC

(57) ABSTRACT

The characterization of a new strain of human rhinovirus of genetic group C (HRV-C) as well as methods and kits for detecting the presence of HRV-C by PCR amplification are provided.

14 Claims, 6 Drawing Sheets

(56) References Cited

OTHER PUBLICATIONS

Renwick et al., "A Recently Identified Rhinovirus Genotype Is Associated with Severe Respiratory-Tract Infection in Children in Germany," *The Journal of Infectious Diseases*, 2007, vol. 196, pp. 1754-1760.

Mcerlean et al., "Characterisation of a newly identified human rhinovirus, HRV-QPM, discovered in infants with bronchiolitis," *Journal of Clinical Virology*, 2007, vol. 39, pp. 67-75.

Xiang et al., "Detection of human rhinovirus genes from clinical sample by one-step RT-PCR," *Chinese Journal of Pediatrics*, 2005, vol. 43, No. 9, pp. 643-647.

Lau et al., "Clinical Features and Complete Genome Characterization of a Distinct Human Rhinovirus (HRV) Genetic Cluster, Probably Representing a Previously Undetected HRV Species, HRV-C, Associated with Acute Respiratory Illness in Children," *Journal of Clinical Microbiology*, 2007, vol. 45, No. 11, pp. 3655-3664.

EMBL accession No. EF512650, Jul. 18, 2007.

Papadopoulos et al., Rhinovirus, "Principles and Practice of Clinical Virology," 2004.

Lee et al., "A Diverse Group of Previously Unrecognized Human Rhinoviruses Are Common Causes of Respiratory Illnesses in Infants," *PloS One*, 2007, No. 10, pp. 1-11.

Ambrose et al., "Virus discovery by sequence-independent genome amplification," *Reviews in Medical Virology*, 2006, vol. 16, pp. 365-383.

Allander et al., "Cloning of a human parvovirus by molecular screening of respiratory tract samples," *PNAS*, 2005, vol. 102, No. 36, pp. 12891-12896.

Allander et al., "Identification of a Third Human Polyomavirus," *Journal of Virology*, 2007, vol. 81, No. 8, pp. 4130-4136.

Gaynor et al., "Identification of a Novel Polyomavirus from Patients with Acute Respiratory Tract Infections," *PloS Pathogens*, 2007, vol. 3, No. 5, pp. 0595-0604.

Stang et al., "Characterization of Virus Isolates by Particle-Associated Nucleic Acid PCR," *Journal of Clinical Microbiology*, 2005, vol. 43, No. 2, pp. 716-720.

Internationrral Search Report in International Application No. PCT/CN2009/071310; dated Jul. 23, 2009.

Written Opinion of the International Searching Authority in International Application No. PCT/CN2009/071310; dated Jul. 23, 2009.

\* cited by examiner

Genomic sequence of BCH019 (SEQ ID NO: 1)

```
tttaaaacagctctgtggttgttcccaccaccaggcacaatgtgcgttgtacactggaatttaggttcctttgtacgcct
gttttcccctcccttaattgtgtgcctttatgtcaaattgcaacttagaagtattttacatgaagccaataggaagcac
cttccccagaggtgtaaaggcaagcacttctgttaccccgggcgtgtgaatacgctttacccaaggctgaagctaaagc
gctcgttatccgcactactactgcgcaatggctagtaggactctggatatgctgtgtcgttttcgctcagcagtgaacccc
cctgtagatcggcgtaatggggctacacaatcccactggcgacagtggtgtaccccgcgtggtgcccgcctgggtcat
agacccaggacgccacagtacagacagggtgtgaagaccggcgtgcgctagttctgaatcctccggccctgaatgcggc
taatcctaaccctgcagccattgcacacaaaccagtgtgtttatggtcgtaatcagtaattgcgggatggaaccgactac
tttgggtgtccgtgtttccttattctttattgtgtgttctcatggttacaattatagtgtaatcatggtgcacaagt
gagtaaacagaatactcgttcgcatgaaaactctgtttcagcttctggaggatcagttataaaatattttaacatcaact
actacaaggattctgctagttcaggcttgacaaaacaagacttctctcaagatccctcaaagtttactcaaccttgggca
gaagcactgacaaatccagcactaatgtcacctagtgttgaagcatgtggatattctgataggctaaagcaaatcactat
cggaaattctacaatcactactcaagacagttttgaacacagttctagcttatgcagaatggccccagtacttatctgata
tagatgcacctctgtcgacaaaccgacccaccctgaaacatcttcagatacattctatactttagatagtgtttgtgtgg
aaacaatcctcattgggcgtggtggtggaaacttccagattgtttgggagaaatcgcggttattttgggcaaaacatgtacta
tcattcaatgggaagatcaggttatgtagtacatgttcagtgtaatgccaccaaattccatagtgggtgtcttatagtag
ccattatcccagagcatcagattgcatatatcggtggtactggagctagagtcaaatataaacatacccacccaggtgat
caaggacatgagcttaaagttttcagttgatagaagtgaccatcaaccagatcaagatccctttttataattgcaatggtac
actgctgggtaatataaccatgttccctcatcagatgattaatctgcgtacaaataattcagctactattgtaataccat
atataaatgctgtacctatggacaacatgttgcggcacaataatgttagtttgctgattataccaattgtcaccctaaga
gccaatggcaatgttgctaacacattgccaataacagtaaccattgctccgcaaaaatcagagttttctggggctatgca
aacccaaaagcaagggctaccaaccagactaccaagtggatctcaacaatttatgactactgaggatgagcaatcaccaa
atatattaccagaatatagccctactaaagagatacatataccaggccagataacaaatattctacacatggctatggtt
cactctttcatccctatgaataatcagcagaaacacaaaggggataaggctatttatcgtgttcaggtaaccgcccagac
aacacacaatggtcttatagttgccataccttttgcagatggataatacattatttagtactactcttttaggtgagatct
taaattatttttcaaattggtcaggggagtataaaaataacatttatgtgtgtgtgactcattcagtactggtaaattt
ttaatggcttatactccacctgggggaaaattacctgaaaccagaaaggatcccatgctgggaacacacctcattgggga
tctgggtttacaatcatcatgtactatggtaataccatggatgagctccactttctaccgtcacactaaatcagataagt
atacatcaggtggctatgttaccttatggtatcagacgaatttgttccaagcatgaatagtggtataggcgttatacta
gctacatgttcacgatgtaaagatttgtctgtaagaatgttaagagacacaccaatgattgaacagcctagtaacaacat
acaaaaccggagaggacttcatcgatgagactctcaaagaggtgttagttgcccaaacacacaaccatcaggaccca
cacatacaaccaaaccaacggcacttggtgccatggagataggggcatcatctcatgctacacctgaatcagtcattgaa
accagatatgttatcaacaatcatacaaataatgaagcattagttgaaaacttccttggtaggtctgcactgtggacgaa
```

Fig. 1

```
cctaacactgaatgcaggttttaagaaatgggagatcaatttccaagagcaggcgcacataaggaagaaacttgaacttt
tcacttacgtgcgcttcgatatggaagttaccatagtgaccaataacacaggcttgatgcagataatgtactcaccacca
ggtattcatccccagaaagtgcaatagataagaaatcggataatcctacaaaccctagtgtttttatcagcctaagag
cggtttccccgctttactataccttccacaggtcttcgctctgcatattatatctttatgatggctatgatgaaactt
ctgaggatgctctaacttatggtatatcagcaactaatgatatggccacactatgttttagagcccttgaggatgaagtg
aaacaaactgttaaagtatacataaaacccaaacatatcaaagcatggtgcccacgaccaccacgtgctgtgaattatac
ccataaatacagtacagattaccacataccaattgaacgaggaagtggaggtcttagagaaagacattactttactttca
gagaagacatcaaaacagcaggacccagtgattattgtacacaccaagagttcatatataaaaatgcccacctgacc
actccaaatgacaatactgtgttattgtcttatagttctgatttacaagtagacacatctagcacaccagggccggattt
catacctacatgtgattgcacagaagggtgttattactcacactctaaagacagatattttgtaatcaaagttaggcct
atgattcgtatgaagttcaagaaaccgtctactaccccaaacatatccaatacaacatgcttattggtgaaggacactgt
cagccacgagattgtggaggtaagttaatgtgtaagcatggtgttattggtataataacagcaggtggggataatcatgt
tgcctttactgacttaagacccttataaatttttgtgcaacgacacaaggcccagtttcagattatctcaatcaacttcgta
atgcctttggtgaagggttcacacagaacattaaggacaactttaatcacatatccagtaatattcaagatcaaattaca
ggaaagattcttaaatggttcgtccgtatcatcagcgcgatgaccattatgatcagaaacagcacagatgttcctacagt
cttagcaactcttgcattgttgggatgccaccatccaccgtggacatttcttaaggataagatatgtaaatggcttcgaa
tccctaaaccgccctccaagcagggtgatggttggctcaaaaaatttacagagtggtgtaatgcagctaaaggattagaa
tgggtgcgtgttaaaataagcaaattcatagattggctaaaggaaaaattgatccctgctgtacagagtaaaagagactt
actcaaagaatgtaaaaagataccctatatcaggagcagatcaacgcttttgctcatgccaaagaagacgcccagaatg
aacttattgtaaatatagacaaacttaagaaaggcctagaccaattagcacctctatatgcagtggagaataaaaaagtc
acagaaatgcaaaaagaattgaaaaggttaagctcctacagaagaactcatcgccatgaaccagtttgccttcttataca
tggagtccctggttgcggtaagtcattgacaacgactcttatagcaaggggtttagccacagaatctgaaatatactcac
taccaccagatcccaaacactttgatggatatgatcaacagaaagttgtgataatggatgatgtaggtcaaaatccagat
ggtcaacatatggggttattttgtcagatggtatccaccacagatttccatgtacctatggctgctattgaagataaagg
taaaagtttcactagtacttatctactagctagtactaatctacaacacttaaatccatctacagtccaaacccacatg
cagtggataggagattttcctggatacagacttaaaaattatgcccaagtttgttaatcaagctgggatgcttaacact
tcacaacacttcaagcatgccagaattgtcccaagcctaaatactacaaccagtgttgcccactattgtgtggcaaggc
agttgttctatacaaccgccggactcaggctagttactccatcaacatggttgtagaacaaatgagggaggaggcaacaa
ctagactcaaggttagacacaatctagatgcaatattccaaggtctaggagattctgagacaccaggcttcataattgat
ttgttatcatcatcaaaagatcctaaagttattcaatactgtgagcataatggcttaatttcacatgcagagagtactat
tgatagacatattaactacacacactacattctaaactgcataggcagtttaattattattttagggacattgtatgcta
tatataaattgatgatagcaacacaaggaccatacacaggattaccacaaaactagtgtcaagaaaccagagttgagcaga
```

```
gcaatacaccagggtcccgaacatgaattcttgtatgcagttattaaaagaaactgtcacataattaccacaaacaaagg
tgatttcaactattaggaatatataataattgtgcagtgatccctactcatgctaactgtggagatacagtacttattg
atggaaaggagataaaagtcctcaaacagtctatcataacagactccaatgatgttgacacagaagttaccataatctgg
ttggacaggaatgaaaaattcagagatatcaggaggtttataccagaaaccatacaagaatggcaccatacaagattagc
aaccaatgtccctaaattcccaatgttcttcgctgatttaggtacaactataccttatggtgaaattaaccttagtggaa
accctacctgtagactcatgaaatatgattaccccactaaaccaggtcagtgtggtgcagtaataggtaacacaggaaac
ataattggtatacatgttggagggaatggaagagttggttactgtgctgctttactgaggaaatactttaatgacaccca
gggtgctatcacacatgtccaagatgttggtgaaagaggattacatccaatcataccccagcaagagcaaattatatc
caagtgttttttatgatgtcttccctggcgtcaaacaacctgcagcccttaatccaagagatccaagattggaaacagat
ctagatactacagtactatcaaaatataaaggtaacaagaaatagaatacaaccagtatatagagacagctgtagatca
ttatacagcccaattatatgtattagacattgaacccaaaccccttacattagagcaagcagtgtatggtatcacaaacc
ttgaacctctggacttaacaactagtgctggttttccgtatgtaactatgggaatcaagaagagggatatcttaaacaag
actactagagatgttacaaaactggaaatgtgtctagaaaagtatggattagatctaccatatataacatttcttaaaga
tgagttaagagctccagagaaaataaaagctggtaagacacgaattatagaagctgcaagcttgaatgacacaacacact
tcagacaggtgtttggaaatcttttcaaaactttccatgccaatcctggtattcttactggttcagctgtaggatgtgac
ccagatatcttttggtcgcagatgtatgtaatgctagatggtgaattacttgcttttgattacacaaattatgatggtag
tttacacccagtgtggttcaaagctcttggtaaggttttggacaacctaggcttccaggagaactcatgaccaagttat
gtaacacaactcacatatacaagaataaaatctacaccacagagggagggatgccatctggcatatgtggtacatccatt
tttaacaccatgatcaacaacatcataatgagaacacttgttttggaaacttataaaaatattgacttagatagattaag
aattatagcatatggtgatgatgttgtagcaagttatccaagtaggttagatccaaaagaaatagcaattacagcttcca
gatatggattaaccatcaccccagcagacaaaagtcaagattttaaaccagtgacttgggaaactgtaactttcttaaa
agacattttataccagataaagaattcaaattcttgatacatcctgtttattcaatgagtgatgtgtatgagtctattag
atggactaaagatcctaaaaatacacaggatcatgttaggtcactatgcatgttagcatggcataatggtaaggagactt
atgaagacttctacagaagataagatcaacttcagtcggaaagaccttggctttaccaccattcacacagttaagacag
cagtggcttgacaatttcatataaatatactacacagatttaatatagaattagtttagtataaaaaaaaaaaaaaaaa
```

Fig. 1 (cont.)

Genomic organization of BCH019 (A) and positions of the 3 different clones obtained by random PCR (B)

Phylogenetic analysis of HRV

PCR products obtained by using primers targeting protein coding regions of BCH019

Fig. 4

SEQUENCE LISTING

<160> NUMBER OF SEQ ID NOS: 23

<210> SEQ ID NO 1
<211> LENGTH: 7121
<212> TYPE: DNA
<213> ORGANISM: Human Rhinovirus BCH019

<400> SEQUENCE: 1

```
tttaaaacag ctgtgtggtt gttcccacca ccaggcacaa tgtgcgttgt acactggaat      60
ttaggttcct ttgtacgcct gttttcccct cccttaattg tgtgccttta tgtcaaattg     120
caacttagaa gtattttaca tgaagcccaa taggaagcac cttccccaga ggtgtaaagg     180
gcaagcactt ctgttacccc gggcgtgtga ataggcttta cccaaggctg aagctaaagc     240
gctcgttatc cgcactacta ctgcgcaatg gctagtagga ctctggatat gctgtgtcgt     300
ttcgctcagc agtgaacccc cctgtagatc ggggtaatgg ggctacacaa tccccactgg     360
cgacagtggt gtagcccgcg tggtgccccg cctgggtcat agacccagga cgccacagta     420
cagacagggt gtgaagaccg gcgtgcgcta gttgtgaatc ctccggcccc tgaatgcggc     480
taatcctaac cctgcagcca ttgcacacaa accagtgtgt ttatggtcgt aatgagtaat     540
tgcgggatgg aaccgactac tttgggtgtc cgtgtttcct ttattctttta ttgtgtgttt     600 ctcatggtta caattatagt gtaatcatgg gtgcacaagt gagtaaacag aatactggtt     660
cgcatgaaaa ctctgtttca gcttctggag gatcagttat aaaatatttt aacatcaact     720
actacaagga ttctgctagt tcaggcttga caaaacaaga cttctctcaa gatccctcaa     780
agtttactca acctttggca gaagcactga caaatccagc actaatgtca cctagtgttg     840
aagcatgtgg atattctgat aggctaaagc aaatcactat cggaaattct acaatcacta     900
ctcaagacag tttgaacaca gttctagctt atggagaatg gccccagtac ttatctgata     960
tagatgcaac ctctgtggac aaaccgaccc accctgaaac atcttcagat agattctata    1020
ctttagatag tgttgtgtgg aaacaatcct cattggggtg tggtggaaa cttccagatt    1080 gtttgggaga aatggggtta tttgggcaaa acatgtacta tcattcaatg ggaagatcag    1140
gttatgtagt acatgttcag tgtaatgcca ccaaattcca tagtgggtgt cttatagtag    1200
ccattatccc agagcatcag attgcatata tcggtggtac tggagctaga gtcaaatata    1260 aacatacca cccaggtgat caaggacatg agcttaaagt ttcagttgat agaagtgacc    1320
atcaaccaga tgaagatccc ttttataatt gcaatggtac actgctgggt aatataacca    1380
tgttccctca tcagatgatt aatctgcgta caaataattc agctactatt gtaataccat    1440 atataaaatgc tgtacctatg gacaacatgt gcggcacaa taatgttagt ttggtgatta    1500
```

```
taccaattgt cacccctaaga gccaatggca atgttgctaa cacattgcca ataacagtaa   1560
ccattgctcc ggaaaaatca gagttttctg gggctatgca aacccaaaag caagggctac   1620
caaccagact accaagtgga tctcaacaat ttatgactac tgaggatgag caatcaccaa   1680
atatattacc agaatatagc cctactaaag agatacatat accaggccag ataacaaata   1740
ttctacacat ggctatggtt cactcttttca tccctatgaa taatcagcag aaacacaaag   1800
gggataaggc tatttatggt gttcaggtaa ccgcccagac aacacacaat ggtcttatag   1860
ttgccatacc tttgcagatg gataatacat tatttagtac tactcttttta ggtgagatct   1920 taaattattt ttcaaattgg tcagggagta taaaaataac atttatgtgt gtgtgtgact   1980
cattcagtac tggtaaattt ttaatggctt atactccacc tgggggaaaa ttacctgaaa   2040
ccagaaagga tgccatgctg gaacacacc tcatttggga tctgggttta caatcatcat   2100
gtactatggt aataccatgg atgagctcca ctttctaccg tcacactaaa tcagataagt   2160
atacatcagg tggctatgtt accttatggt atcagacgaa ttttgttcca agcatgaata   2220
gtggtatagg cgttatacta gctacatgtt caggatgtaa agatttgtct gtaagaatgt   2280
taagagacac accaatgatt gaacagccta gtaacaacat acaaaacccg gtagaggact   2340
tcatcgatga gactctcaaa gaggtgttag ttgtcccaaa cacacaacca tcaggaccca   2400 cacatacaaac caaccaacg gcacttggtg ccatggagat aggggcaaca tctgatgcta   2460
cacctgaatc agtcattgaa accagatatg ttatcaacaa tcatacaaat aatgaagcat   2520
tagttgaaaa cttccttggt aggtctgcac tgtggacgaa cctaacactg aatgcaggtt   2580
ttaagaaatg ggagatcaat ttccaagagc aggcgcacat aaggaagaaa cttgaactttt   2640 tcacttacgt gcgcttcgat atggaagtta ccatagtgac caataacaca ggcttgatgc   2700
agataatgta ctcaccacca ggtattgatc ccccagaaag tgcaatagat aagaaatggg   2760
ataatgctac aaaccctagt gttttttatc agcctaagag cggttttccccc cgctttacta   2820 tacctttcac aggtcttggc tctgcatatt atatcttttta tgatggctat gatgaaactt   2880
ctgaggatgc tctaacttat ggtatatcag caactaatga tatgggcaca ctatgttttta   2940 gagcccttga ggatgaagtg aaacaaactg ttaaagtata cataaaaccc aaacatatca   3000
aagcatggtg cccacgacca ccacgtgctg tgaattatac ccataaatac agtacagatt   3060
accacatacc aattgaagga ggaagtggag gtcttagaga aagacattac tttactttca   3120
gagaagacat caaaacagca ggacccagtg atttatttgt acacacccaa gagttcatat   3180
ataaaaatgc ccacctgacc actccaaatg acaatactgt gttattgtct tatagttctg   3240
atttacaagt agacacatct agcacaccag ggccggattt catacctaca tgtgattgca   3300
cagaagggtg ttattactca cactctaaag acagatattt tgtaatcaaa gttagggcct   3360
atgattggta tgaagttcaa gaaaccgtct actaccccaa acatatccaa tacaacatgc   3420
ttattggtga aggacactgt cagccaggag attgtggagg taagttaatg tgtaagcatg   3480
gtgttattgg tataataaca gcaggtgggg ataatcatgt tgcctttact gacttaagac   3540
cttataaatt ttgtgcaacg acacaaggcc cagtttcaga ttatctcaat caacttggta   3600
atgcctttgg tgaagggttc acacagaaca ttaaggacaa cttttaatcac atatccagta   3660 atattcaaga tcaaattaca ggaaagattc ttaaatggtt cgtccgtatc atcagcgcga   3720
tgaccattat gatcagaaac agcacagatg ttcctacagt cttagcaact cttgcattgt   3780
tgggatgcca ccattcaccg tggacatttc ttaaggataa gatatgtaaa tggcttggaa   3840
tccctaaacc gccctccaag cagggtgatg gttggctcaa aaaatttaca gagtggtgta   3900
```

```
atgcagctaa aggattagaa tgggtgggtg ttaaaataag caaattcata gattggctaa    3960
aggaaaaatt gatccctgct gtacagagta aaagagactt actcaaagaa tgtaaaaaga    4020
taccettata tcaggagcag atcaaggctt ttgctcatgc caaagaagac gcccagaatg    4080
aacttattgt aaatatagac aaacttaaga aaggcctaga ccaattagca cctctatatg    4140
cagtggagaa taaaaaagtc acagaaatgc aaaagaatt gaaaaggtta agctcctaca     4200
gaagaactca tcgccatgaa ccagtttgcc ttcttataca tggagtgcct ggttgcggta    4260
agtcattgac aacgactgtt atagcaaggg gtttagccac agaatctgaa atatactcac    4320
taccaccaga tcccaaacac tttgatggat atgatcaaca gaaagttgtg ataatggatg    4380
atgtaggtca aaatccagat ggtcaagata tggggttatt ttgtcagatg gtatccacca    4440
cagatttcca tgtacctatg gctgctattg aagataaagg taaagtttc actagtactt     4500
atctactagc tagtactaat ctacaacact aaatccatc tacagtccaa accccagatg     4560
cagtggatag gagattttc ctggatacag acttaaaaat tatgcccaag tttgttaatc     4620
aagctgggat gcttaacact tcacaagcac ttcaagcatg ccagaattgt cccaagccta    4680
aatactacaa ccagtgttgc ccactattgt gtggcaaggc agttgttcta tacaaccgcc    4740
ggactcaggc tagttactcc atcaacatgg ttgtagaaca aatgagggag gaggcaacaa    4800
ctagactcaa ggttagacac aatctagatg caatattcca aggtctagga gattctgaga    4860
caccaggctt cataattgat ttgttatcat catcaaaaga tcctaaagtt attcaatact    4920
gtgaggataa tggcttaatt tcacatgcag agagtagtat tgatagacat attaactaca    4980
cacactacat tctaaactgc ataggcagtt taattattat tttagggaca ttgtatgcta    5040
tatataaatt gatgatagca acacaaggac catacacagg attaccacaa actagtgtca    5100
agaaaccaga gttgaggaga gcaatacacc agggtcccga acatgaattc ttgtatgcag    5160
ttattaaaag aaactgtcac ataattacca caaacaaagg tgatttcaac ttattaggaa    5220
tatataataa ttgtgcagtg atccctactc atgctaactg tggagataca gtacttattg    5280
atggaaagga gataaaagtc ctcaaacagt ctatcataac agactccaat gatgttgaca    5340
cagaagttac cataatctgg ttggacagga tgaaaaatt cagagatatc aggagggttta    5400
taccagaaac catacaagaa tggcaccata caagattagc aaccaatgtc cctaaattcc    5460
caatgttctt cgctgattta ggtacaacta taccttatgg tgaaattaac cttagtggaa    5520
accctacctg tagactcatg aaatatgatt accccactaa accaggtcag tgtggtgcag    5580
taataggtaa cacaggaaac ataattggta tacatgttgg agggaatgga agagttggtt    5640
actgtgctgc tttactgagg aaatacttta tgacaccca gggtgctatc acacatgtcc     5700
aagatgttgg tgaaagagga ttacatccaa tcaataccc cagcaagagc aaattatatc     5760
caagtgtttt ttatgatgtc ttccctggcg tcaaacaacc tgcagccctt aatccaagag    5820
atccaagatt ggaaacagat ctagatacta cagtactatc aaaatataaa ggtaacaaag    5880
aaatagaata caaccagtat atagagacag ctgtagatca ttatacagcc caattatatg    5940
tattagacat tgaacccaaa ccccttacat tagagcaagc agtgtatggt atcacaaacc    6000
ttgaacctct ggacttaaca actagtgctg gttttccgta tgtaactatg ggaatcaaga    6060
agagggatat cttaaacaag actactgagg atgttacaaa actggaaatg tgtctagaaa    6120
agtatggatt agatctacca tatataacat ttcttaaaga tgagttaaga gctccagaga    6180
aaataaaagc tggtaagaca cgaattatag aagctgcaag cttgaatgac acaacacact    6240
tcagacaggt gttggaaat cttttcaaaa cttcccatgc caatcctggt attcttactg      6300
```

-continued

```
gttcagctgt aggatgtgac ccagatatct tttggtcgca gatgtatgta atgctagatg    6360
gtgaattact tgcttttgat tacacaaatt atgatggtag tttacaccca gtgtggttca    6420
aagctcttgg taaggttttg gacaacctag gctttccagg agaactcatg accaagttat    6480
gtaacacaac tcacatatac aagaataaaa tctacaccac agagggaggg atgccatctg    6540
gcatatgtgg tacatccatt tttaacacca tgatcaacaa catcataatg agaacacttg    6600
ttttggaaac ttataaaaat attgacttag atagattaag aattatagca tatggtgatg    6660
atgttgtagc aagttatcca agtaggttag atccaaaaga aatagcaatt acagcttcca    6720
gatatggatt aaccatcacc ccagcagaca aaagtcaaga ttttaaacca gtgacttggg    6780
aaactgtaac ttttcttaaa agacatttta taccagataa agaattcaaa ttcttgatac    6840
atcctgttta ttcaatgagt gatgtgtatg agtctattag atggactaaa gatcctaaaa    6900
atacacagga tcatgttagg tcactatgca tgttagcatg gcataatggt aaggagactt    6960
atgaagactt tctacagaag ataagatcaa cttcagtcgg aaagaccttg gctttaccac    7020
cattcacaca gttaagacag cagtggcttg acaatttcat ataaatatac tacacagatt    7080
taatatagaa ttagtttagt ataaaaaaaa aaaaaaaaa a    7121
```

<210> SEQ ID NO 2
<211> LENGTH: 26
<212> TYPE: DNA
<213> ORGANISM: Artificial Sequence
<220> FEATURE:
<223> OTHER INFORMATION: Synthetic Construct - Primer
<220> FEATURE:
<221> NAME/KEY: misc_feature
<222> LOCATION: (21)..(26)
<223> OTHER INFORMATION: n is a, c, g, or t

<400> SEQUENCE: 2
gccggagctc tgcagatatc nnnnnn    26

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 3
gccggagctc tgcagatatc    20

<210> SEQ ID NO 4
<211> LENGTH: 24
<212> TYPE: DNA
<213> ORGANISM: Artificial Sequence
<220> FEATURE:
<223> OTHER INFORMATION: Synthetic Construct - Primer

<400> SEQUENCE: 4
cgccagggtt ttcccagtca cgac    24

<210> SEQ ID NO 5
<211> LENGTH: 24
<212> TYPE: DNA
<213> ORGANISM: Artificial Sequence
<220> FEATURE:
<223> OTHER INFORMATION: Synthetic Construct - Primer

<400> SEQUENCE: 5
gagcggataa caatttcaca cagg    24

<210> SEQ ID NO 6
<211> LENGTH: 23
<212> TYPE: DNA
<213> ORGANISM: Artificial Sequence
<220> FEATURE:
<223> OTHER INFORMATION: Synthetic Construct - Primer

<400> SEQUENCE: 6
actactttgg gtgtccgtgt ttc                                              23

<210> SEQ ID NO 7
<211> LENGTH: 25
<212> TYPE: DNA
<213> ORGANISM: Artificial Sequence
<220> FEATURE:
<223> OTHER INFORMATION: Synthetic Construct - Primer

<400> SEQUENCE: 7
tttccratag tgatttgctt kagcc                                            25

<210> SEQ ID NO 8
<211> LENGTH: 20
<212> TYPE: DNA
<213> ORGANISM: Artificial Sequence
<220> FEATURE:
<223> OTHER INFORMATION: Synthetic Construct - Primer

<400> SEQUENCE: 8
atgggtgcac aagtgagtaa                                                  20

<210> SEQ ID NO 9
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 9
gctattgctt ttgggtttg                                                   19

<210> SEQ ID NO 10
<211> LENGTH: 22
<212> TYPE: DNA
<213> ORGANISM: Artificial Sequence
<220> FEATURE:
<223> OTHER INFORMATION: Synthetic Construct - Primer

<400> SEQUENCE: 10
gggctaccaa ccagactacc aa                                               22

<210> SEQ ID NO 11
<211> LENGTH: 24
<212> TYPE: DNA
<213> ORGANISM: Artificial Sequence
<220> FEATURE:
<223> OTHER INFORMATION: Synthetic Construct - Primer

<400> SEQUENCE: 11
cgatatgttg ttactaggct gttc                                             24

<210> SEQ ID NO 12
<211> LENGTH: 23
<212> TYPE: DNA
<213> ORGANISM: Artificial Sequence
<220> FEATURE:
<223> OTHER INFORMATION: Synthetic Construct - Primer -continued

```
<400> SEQUENCE: 12
ggacccagtg atttatttgt aca                                           23

<210> SEQ ID NO 13
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 13
ctgcttggag ggcggttta                                                19

<210> SEQ ID NO 14
<211> LENGTH: 19
<212> TYPE: DNA
<213> ORGANISM: Artificial Sequence
<220> FEATURE:
<223> OTHER INFORMATION: Synthetic Construct - Primer

<400> SEQUENCE: 14
cagtggtgat ggttggctc                                                19

<210> SEQ ID NO 15
<211> LENGTH: 21
<212> TYPE: DNA
<213> ORGANISM: Artificial Sequence
<220> FEATURE:
<223> OTHER INFORMATION: Synthetic Construct - Primer

<400> SEQUENCE: 15
gcgttggaat attgcatcta g                                             21

<210> SEQ ID NO 16
<211> LENGTH: 23
<212> TYPE: DNA
<213> ORGANISM: Artificial Sequence
<220> FEATURE:
<223> OTHER INFORMATION: Synthetic Construct - Primer

<400> SEQUENCE: 16
gattaggaga ttctgagaca cca                                           23

<210> SEQ ID NO 17
<211> LENGTH: 22
<212> TYPE: DNA
<213> ORGANISM: Artificial Sequence
<220> FEATURE:
<223> OTHER INFORMATION: Synthetic Construct - Primer

<400> SEQUENCE: 17
cgctgggtgt cattaaagta tt                                            22

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct - Primer

<400> SEQUENCE: 18
tgctatcaca catgtccaag a                                             21

<210> SEQ ID NO 19
<211> LENGTH: 19
<212> TYPE: DNA
```

-continued

<213> ORGANISM: Artificial Sequence
<220> FEATURE:
<223> OTHER INFORMATION: Synthetic Construct - Primer

<400> SEQUENCE: 19
gaaattgtca agccactgc                                                   19

<210> SEQ ID NO 20
<211> LENGTH: 2145
<212> TYPE: PRT
<213> ORGANISM: Human Rhinovirus BCH019

<400> SEQUENCE: 20

```
Met Gly Ala Gln Val Ser Lys Gln Asn Thr Gly Ser His Glu Asn Ser
1               5                   10                  15

Val Ser Ala Ser Gly Gly Ser Val Ile Lys Tyr Phe Asn Ile Asn Tyr
            20                  25                  30

Tyr Lys Asp Ser Ala Ser Ser Gly Leu Thr Lys Gln Asp Phe Ser Gln
        35                  40                  45

Asp Pro Ser Lys Phe Thr Gln Pro Leu Ala Glu Ala Leu Thr Asn Pro
    50                  55                  60

Ala Leu Met Ser Pro Ser Val Glu Ala Cys Gly Tyr Ser Asp Arg Leu
65                  70                  75                  80

Lys Gln Ile Thr Ile Gly Asn Ser Thr Ile Thr Thr Gln Asp Ser Leu
                85                  90                  95

Asn Thr Val Leu Ala Tyr Gly Glu Trp Pro Gln Tyr Leu Ser Asp Ile
            100                 105                 110

Asp Ala Thr Ser Val Asp Lys Pro Thr His Pro Glu Thr Ser Ser Asp
        115                 120                 125

Arg Phe Tyr Thr Leu Asp Ser Val Val Trp Lys Gln Ser Ser Leu Gly
    130                 135                 140

Trp Trp Trp Lys Leu Pro Asp Cys Leu Gly Glu Met Gly Leu Phe Gly
145                 150                 155                 160

Gln Asn Met Tyr Tyr His Ser Met Gly Arg Ser Gly Tyr Val Val His
                165                 170                 175

Val Gln Cys Asn Ala Thr Lys Phe His Ser Gly Cys Leu Ile Val Ala
            180                 185                 190

Ile Ile Pro Glu His Gln Ile Ala Tyr Ile Gly Gly Thr Gly Ala Arg
        195                 200                 205

Val Lys Tyr Lys His Thr His Pro Gly Asp Gln Gly His Glu Leu Lys
    210                 215                 220

Val Ser Val Asp Arg Ser Asp His Gln Pro Asp Glu Asp Pro Phe Tyr
225                 230                 235                 240

Asn Cys Asn Gly Thr Leu Leu Gly Asn Ile Thr Met Phe Pro His Gln
                245                 250                 255

Met Ile Asn Leu Arg Thr Asn Asn Ser Ala Thr Ile Val Ile Pro Tyr
            260                 265                 270

Ile Asn Ala Val Pro Met Asp Asn Met Leu Arg His Asn Asn Val Ser
        275                 280                 285

Leu Val Ile Ile Pro Ile Val Thr Leu Arg Ala Asn Gly Asn Val Ala
    290                 295                 300

Asn Thr Leu Pro Ile Thr Val Thr Ile Ala Pro Glu Lys Ser Glu Phe
305                 310                 315                 320

Ser Gly Ala Met Gln Thr Gln Lys Gln Gly Leu Pro Thr Arg Leu Pro
                325                 330                 335

Ser Gly Ser Gln Gln Phe Met Thr Thr Glu Asp Glu Gln Ser Pro Asn
```

```
                340             345             350
Ile Leu Pro Glu Tyr Ser Pro Thr Lys Glu Ile His Ile Pro Gly Gln
            355             360             365

Ile Thr Asn Ile Leu His Met Ala Met Val His Ser Phe Ile Pro Met
        370             375             380

Asn Asn Gln Gln Lys His Lys Gly Asp Lys Ala Ile Tyr Gly Val Gln
385             390             395             400

Val Thr Ala Gln Thr Thr His Asn Gly Leu Ile Val Ala Ile Pro Leu
            405             410             415

Gln Met Asp Asn Thr Leu Phe Ser Thr Thr Leu Leu Gly Glu Ile Leu
            420             425             430

Asn Tyr Phe Ser Asn Trp Ser Gly Ser Ile Lys Ile Thr Phe Met Cys
            435             440             445

Val Cys Asp Ser Phe Ser Thr Gly Lys Phe Leu Met Ala Tyr Thr Pro
            450             455             460

Pro Gly Gly Lys Leu Pro Glu Thr Arg Lys Asp Ala Met Leu Gly Thr
465             470             475             480

His Leu Ile Trp Asp Leu Gly Leu Gln Ser Ser Cys Thr Met Val Ile
            485             490             495

Pro Trp Met Ser Ser Thr Phe Tyr Arg His Thr Lys Ser Asp Lys Tyr
            500             505             510

Thr Ser Gly Gly Tyr Val Thr Leu Trp Tyr Gln Thr Asn Phe Val Pro
            515             520             525

Ser Met Asn Ser Gly Ile Gly Val Ile Leu Ala Thr Cys Ser Gly Cys
            530             535             540

Lys Asp Leu Ser Val Arg Met Leu Arg Asp Thr Pro Met Ile Glu Gln
545             550             555             560

Pro Ser Asn Asn Ile Gln Asn Pro Val Glu Asp Phe Ile Asp Glu Thr
            565             570             575

Leu Lys Glu Val Leu Val Val Pro Asn Thr Gln Pro Ser Gly Pro Thr
            580             585             590

His Thr Thr Lys Pro Thr Ala Leu Gly Ala Met Glu Ile Gly Ala Thr
            595             600             605

Ser Asp Ala Thr Pro Glu Ser Val Ile Glu Thr Arg Tyr Val Ile Asn
            610             615             620

Asn His Thr Asn Asn Glu Ala Leu Val Glu Asn Phe Leu Gly Arg Ser
625             630             635             640

Ala Leu Trp Thr Asn Leu Thr Leu Asn Ala Gly Phe Lys Lys Trp Glu
            645             650             655

Ile Asn Phe Gln Glu Gln Ala His Ile Arg Lys Lys Leu Glu Leu Phe
            660             665             670

Thr Tyr Val Arg Phe Asp Met Glu Val Thr Ile Val Thr Asn Asn Thr
            675             680             685

Gly Leu Met Gln Ile Met Tyr Ser Pro Pro Gly Ile Asp Pro Pro Glu
            690             695             700

Ser Ala Ile Asp Lys Lys Trp Asp Asn Ala Thr Asn Pro Ser Val Phe
705             710             715             720

Tyr Gln Pro Lys Ser Gly Phe Pro Arg Phe Thr Ile Pro Phe Thr Gly
            725             730             735

Leu Gly Ser Ala Tyr Tyr Ile Phe Tyr Asp Gly Tyr Asp Glu Thr Ser
            740             745             750

Glu Asp Ala Leu Thr Tyr Gly Ile Ser Ala Thr Asn Asp Met Gly Thr
            755             760             765
```

-continued

```
Leu Cys Phe Arg Ala Leu Glu Asp Glu Val Lys Gln Thr Val Lys Val
            770                 775                 780

Tyr Ile Lys Pro Lys His Ile Lys Ala Trp Cys Arg Pro Pro Arg
785                 790                 795                 800

Ala Val Asn Tyr Thr His Lys Tyr Ser Thr Asp Tyr His Ile Pro Ile
                805                 810                 815

Glu Gly Gly Ser Gly Gly Leu Arg Glu Arg His Tyr Phe Thr Phe Arg
                820                 825                 830

Glu Asp Ile Lys Thr Ala Gly Pro Ser Asp Leu Phe Val His Thr Gln
                835                 840                 845

Glu Phe Ile Tyr Lys Asn Ala His Leu Thr Thr Pro Asn Asp Asn Thr
            850                 855                 860

Val Leu Leu Ser Tyr Ser Ser Asp Leu Gln Val Asp Thr Ser Ser Thr
865                 870                 875                 880

Pro Gly Pro Asp Phe Ile Pro Thr Cys Asp Cys Thr Glu Gly Cys Tyr
                885                 890                 895

Tyr Ser His Ser Lys Asp Arg Tyr Phe Val Ile Lys Val Arg Ala Tyr
                900                 905                 910

Asp Trp Tyr Glu Val Gln Glu Thr Val Tyr Tyr Pro Lys His Ile Gln
            915                 920                 925

Tyr Asn Met Leu Ile Gly Glu Gly His Cys Gln Pro Gly Asp Cys Gly
            930                 935                 940

Gly Lys Leu Met Cys Lys His Gly Val Ile Gly Ile Ile Thr Ala Gly
945                 950                 955                 960

Gly Asp Asn His Val Ala Phe Thr Asp Leu Arg Pro Tyr Lys Phe Cys
                965                 970                 975

Ala Thr Thr Gln Gly Pro Val Ser Asp Tyr Leu Asn Gln Leu Gly Asn
                980                 985                 990

Ala Phe Gly Glu Gly Phe Thr Gln Asn Ile Lys Asp Asn Phe Asn His
            995                 1000                1005

Ile Ser Ser Asn Ile Gln Asp Gln Ile Thr Gly Lys Ile Leu Lys
    1010                1015                1020

Trp Phe Val Arg Ile Ile Ser Ala Met Thr Ile Met Ile Arg Asn
    1025                1030                1035

Ser Thr Asp Val Pro Thr Val Leu Ala Thr Leu Ala Leu Leu Gly
    1040                1045                1050

Cys His His Ser Pro Trp Thr Phe Leu Lys Asp Lys Ile Cys Lys
    1055                1060                1065

Trp Leu Gly Ile Pro Lys Pro Pro Ser Lys Gln Gly Asp Gly Trp
    1070                1075                1080

Leu Lys Lys Phe Thr Glu Trp Cys Asn Ala Ala Lys Gly Leu Glu
    1085                1090                1095

Trp Val Gly Val Lys Ile Ser Lys Phe Ile Asp Trp Leu Lys Glu
    1100                1105                1110

Lys Leu Ile Pro Ala Val Gln Ser Lys Arg Asp Leu Leu Lys Glu
    1115                1120                1125

Cys Lys Lys Ile Pro Leu Tyr Gln Glu Gln Ile Lys Ala Phe Ala
    1130                1135                1140

His Ala Lys Glu Asp Ala Gln Asn Glu Leu Ile Val Asn Ile Asp
    1145                1150                1155

Lys Leu Lys Lys Gly Leu Asp Gln Leu Ala Pro Leu Tyr Ala Val
    1160                1165                1170

Glu Asn Lys Lys Val Thr Glu Met Gln Lys Glu Leu Lys Arg Leu
    1175                1180                1185
```

```
Ser Ser Tyr Arg Arg Thr His Arg His Glu Pro Val Cys Leu Leu
    1190            1195                1200

Ile His Gly Val Pro Gly Cys Gly Lys Ser Leu Thr Thr Thr Val
    1205            1210                1215

Ile Ala Arg Gly Leu Ala Thr Glu Ser Glu Ile Tyr Ser Leu Pro
    1220            1225                1230

Pro Asp Pro Lys His Phe Asp Gly Tyr Asp Gln Gln Lys Val Val
    1235            1240                1245

Ile Met Asp Asp Val Gly Gln Asn Pro Asp Gly Gln Asp Met Gly
    1250            1255                1260

Leu Phe Cys Gln Met Val Ser Thr Thr Asp Phe His Val Pro Met
    1265            1270                1275

Ala Ala Ile Glu Asp Lys Gly Lys Ser Phe Thr Ser Thr Tyr Leu
    1280            1285                1290

Leu Ala Ser Thr Asn Leu Gln His Leu Asn Pro Ser Thr Val Gln
    1295            1300                1305

Thr Pro Asp Ala Val Asp Arg Arg Phe Phe Leu Asp Thr Asp Leu
    1310            1315                1320

Lys Ile Met Pro Lys Phe Val Asn Gln Ala Gly Met Leu Asn Thr
    1325            1330                1335

Ser Gln Ala Leu Gln Ala Cys Gln Asn Cys Pro Lys Pro Lys Tyr
    1340            1345                1350

Tyr Asn Gln Cys Cys Pro Leu Leu Cys Gly Lys Ala Val Val Leu
    1355            1360                1365

Tyr Asn Arg Arg Thr Gln Ala Ser Tyr Ser Ile Asn Met Val Val
    1370            1375                1380

Glu Gln Met Arg Glu Ala Thr Thr Arg Leu Lys Val Arg His
    1385            1390                1395

Asn Leu Asp Ala Ile Phe Gln Gly Leu Gly Asp Ser Glu Thr Pro
    1400            1405                1410

Gly Phe Ile Ile Asp Leu Leu Ser Ser Ser Lys Asp Pro Lys Val
    1415            1420                1425

Ile Gln Tyr Cys Glu Asp Asn Gly Leu Ile Ser His Ala Glu Ser
    1430            1435                1440

Ser Ile Asp Arg His Ile Asn Tyr Thr His Tyr Ile Leu Asn Cys
    1445            1450                1455

Ile Gly Ser Leu Ile Ile Ile Leu Gly Thr Leu Tyr Ala Ile Tyr
    1460            1465                1470

Lys Leu Met Ile Ala Thr Gln Gly Pro Tyr Thr Gly Leu Pro Gln
    1475            1480                1485

Thr Ser Val Lys Lys Pro Glu Leu Arg Arg Ala Ile His Gln Gly
    1490            1495                1500

Pro Glu His Glu Phe Leu Tyr Ala Val Ile Lys Arg Asn Cys His
    1505            1510                1515

Ile Ile Thr Thr Asn Lys Gly Asp Phe Asn Leu Leu Gly Ile Tyr
    1520            1525                1530

Asn Asn Cys Ala Val Ile Pro Thr His Ala Asn Cys Gly Asp Thr
    1535            1540                1545

Val Leu Ile Asp Gly Lys Glu Ile Lys Val Leu Lys Gln Ser Ile
    1550            1555                1560

Ile Thr Asp Ser Asn Asp Val Asp Thr Glu Val Thr Ile Ile Trp
    1565            1570                1575

Leu Asp Arg Asn Glu Lys Phe Arg Asp Ile Arg Arg Phe Ile Pro
```

-continued

```
            1580                1585                1590
Glu Thr Ile Gln Glu Trp His His Thr Arg Leu Ala Thr Asn Val
    1595                1600                1605
Pro Lys Phe Pro Met Phe Phe Ala Asp Leu Gly Thr Thr Ile Pro
    1610                1615                1620
Tyr Gly Glu Ile Asn Leu Ser Gly Asn Pro Thr Cys Arg Leu Met
    1625                1630                1635
Lys Tyr Asp Tyr Pro Thr Lys Pro Gly Gln Cys Gly Ala Val Ile
    1640                1645                1650
Gly Asn Thr Gly Asn Ile Ile Gly Ile His Val Gly Gly Asn Gly
    1655                1660                1665
Arg Val Gly Tyr Cys Ala Ala Leu Leu Arg Lys Tyr Phe Asn Asp
    1670                1675                1680
Thr Gln Gly Ala Ile Thr His Val Gln Asp Val Gly Glu Arg Gly
    1685                1690                1695
Leu His Pro Ile Asn Thr Pro Ser Lys Ser Lys Leu Tyr Pro Ser
    1700                1705                1710
Val Phe Tyr Asp Val Phe Pro Gly Val Lys Gln Pro Ala Ala Leu
    1715                1720                1725
Asn Pro Arg Asp Pro Arg Leu Glu Thr Asp Leu Asp Thr Thr Val
    1730                1735                1740
Leu Ser Lys Tyr Lys Gly Asn Lys Glu Ile Glu Tyr Asn Gln Tyr
    1745                1750                1755
Ile Glu Thr Ala Val Asp His Tyr Thr Ala Gln Leu Tyr Val Leu
    1760                1765                1770
Asp Ile Glu Pro Lys Pro Leu Thr Leu Glu Gln Ala Val Tyr Gly
    1775                1780                1785
Ile Thr Asn Leu Glu Pro Leu Asp Leu Thr Thr Ser Ala Gly Phe
    1790                1795                1800
Pro Tyr Val Thr Met Gly Ile Lys Lys Arg Asp Ile Leu Asn Lys
    1805                1810                1815
Thr Thr Arg Asp Val Thr Lys Leu Glu Met Cys Leu Glu Lys Tyr
    1820                1825                1830
Gly Leu Asp Leu Pro Tyr Ile Thr Phe Leu Lys Asp Glu Leu Arg
    1835                1840                1845
Ala Pro Glu Lys Ile Lys Ala Gly Lys Thr Arg Ile Ile Glu Ala
    1850                1855                1860
Ala Ser Leu Asn Asp Thr Thr His Phe Arg Gln Val Phe Gly Asn
    1865                1870                1875
Leu Phe Lys Thr Phe His Ala Asn Pro Gly Ile Leu Thr Gly Ser
    1880                1885                1890
Ala Val Gly Cys Asp Pro Asp Ile Phe Trp Ser Gln Met Tyr Val
    1895                1900                1905
Met Leu Asp Gly Glu Leu Leu Ala Phe Asp Tyr Thr Asn Tyr Asp
    1910                1915                1920
Gly Ser Leu His Pro Val Trp Phe Lys Ala Leu Gly Lys Val Leu
    1925                1930                1935
Asp Asn Leu Gly Phe Pro Gly Glu Leu Met Thr Lys Leu Cys Asn
    1940                1945                1950
Thr Thr His Ile Tyr Lys Asn Lys Ile Tyr Thr Thr Glu Gly Gly
    1955                1960                1965
Met Pro Ser Gly Ile Cys Gly Thr Ser Ile Phe Asn Thr Met Ile
    1970                1975                1980
```

```
Asn Asn Ile Ile Met Arg Thr Leu Val Leu Glu Thr Tyr Lys Asn
    1985            1990                1995

Ile Asp Leu Asp Arg Leu Arg Ile Ile Ala Tyr Gly Asp Asp Val
    2000            2005                2010

Val Ala Ser Tyr Pro Ser Arg Leu Asp Pro Lys Glu Ile Ala Ile
    2015            2020                2025

Thr Ala Ser Arg Tyr Gly Leu Thr Ile Thr Pro Ala Asp Lys Ser
    2030            2035                2040

Gln Asp Phe Lys Pro Val Thr Trp Glu Thr Val Thr Phe Leu Lys
    2045            2050                2055

Arg His Phe Ile Pro Asp Lys Glu Phe Lys Phe Leu Ile His Pro
    2060            2065                2070

Val Tyr Ser Met Ser Asp Val Tyr Glu Ser Ile Arg Trp Thr Lys
    2075            2080                2085

Asp Pro Lys Asn Thr Gln Asp His Val Arg Ser Leu Cys Met Leu
    2090            2095                2100

Ala Trp His Asn Gly Lys Glu Thr Tyr Glu Asp Phe Leu Gln Lys
    2105            2110                2115

Ile Arg Ser Thr Ser Val Gly Lys Thr Leu Ala Leu Pro Pro Phe
    2120            2125                2130

Thr Gln Leu Arg Gln Gln Trp Leu Asp Asn Phe Ile
    2135            2140                2145

<210> SEQ ID NO 21
<211> LENGTH: 201
<212> TYPE: DNA
<213> ORGANISM: Human Rhinovirus BCH019

<400> SEQUENCE: 21
atgggtgcac aagtgagtaa acagaatact ggttcgcatg aaaactctgt ttcagcttct    60
ggaggatcag ttataaaata ttttaacatc aactactaca aggattctgc tagttcaggc   120
ttgacaaaac aagacttctc tcaagatccc tcaaagttta ctcaacccttt ggcagaagca   180 ctgacaaatc cagcactaat g                                              201

<210> SEQ ID NO 22
<211> LENGTH: 786
<212> TYPE: DNA
<213> ORGANISM: Human Rhinovirus BCH019

<400> SEQUENCE: 22
tcacctagtg ttgaagcatg tggatattct gataggctaa agcaaatcac tatcggaaat    60
tctacaatca ctactcaaga cagtttgaac acagttctag cttatggaga atggccccag   120
tacttatctg atatagatgc aacctctgtg acaaaccga cccaccctga acatcttca     180 gatagattct atactttaga tagtgttgtg tggaaacaat cctcattggg gtggtggtgg   240
aaacttccag attgtttggg agaaatgggg ttatttgggc aaaacatgta ctatcattca   300
atgggaagat caggttatgt agtacatgtt cagtgtaatg ccaccaaatt ccatagtggg   360
tgtcttatag tagccattat cccagagcat cagattgcat atatcggtgg tactggagct   420
agagtcaaat ataaacatac ccacccaggt gatcaaggac atgagcttaa agtttcagtt   480
gatagaagtg accatcaacc agatgaagat ccctttttata attgcaatgg tacactgctg   540
ggtaatataa ccatgttccc tcatcagatg attaatctgc gtacaaataa ttcagctact   600 attgtaaatac catatataaa tgctgtacct atggacaaca tgttgcggca caataatgtt   660
agtttggtga ttataccaat tgtcacccta agagccaatg gcaatgttgc taacacattg   720
```

```
ccaataacag taaccattgc tccggaaaaa tcagagtttt ctggggctat gcaaacccaa    780
aagcaa                                                              786

<210> SEQ ID NO 23
<211> LENGTH: 331
<212> TYPE: DNA
<213> ORGANISM: Human Rhinovirus BCH019

<400> SEQUENCE: 23
actactttgg gtgtccgtgt ttcctttatt ctttattgtg tgtttctcat ggttacaatt     60
atagtgtaat catgggtgca caagtgagta aacagaatac tggttcgcat gaaaactctg    120
tttcagcttc tggaggatca gttataaaat attttaacat caactactac aaggattctg    180
ctagttcagg cttgacaaaa caagacttct ctcaagatcc ctcaaagttt actcaacctt    240
tggcagaagc actgacaaat ccagcactaa tgtcacctag tgttgaagca tgtggatatt    300
ctgataggct aaagcaaatc actatcggaa a                                   331
```

NEWLY IDENTIFIED HUMAN RHINOVIRUS OF HRV-C AND METHODS AND KITS FOR DETECTING HRV-CS

CROSS-REFERENCE TO RELATED APPLICATIONS

The present application is a national stage entry of PCT/CN2009/071310, filed Apr. 16, 2009, which claims priority to PCT/CN2008/000785, filed Apr. 17, 2008.

FIELD OF THE INVENTION

The present invention generally relates to the identification and detection of human rhinoviruses. More particularly, the present invention relates to the characterization of a new strain of human rhinovirus of genetic group C (HRV-C) as well as methods and kits for detecting the presence of HRV-C, for instance, by PCR amplification.

BACKGROUND OF THE INVENTION

Human rhinoviruses (HRVs) are the major cause of common cold. Although the majority of HRV infections only cause mild disease, Rhinoviruses can also cause lower respiratory tract infections resulting in severe disease in children, in the elderly and in immunosuppressed patients. Their impact on overall morbidity and their economic cost worldwide are considerable.

Rhinoviruses are small RNA, non-enveloped, viruses belonging to the family picornaviridae. Until now, over 100 serotypes of Rhinoviruses have been identified by specific antisera in a collaborative program supported by the World Health Organization (WHO). Rhinoviruses are divided into major (90%) and minor (10%) groups, according to their cellular receptor usage. An alternative classification, dividing the viruses into group A and B, based on sensitivity to antiviral compounds and correlating with sequence similarities and pathogenicity, has also been proposed[1].

In recent years, some researchers have identified new rhinoviruses which cannot be classified into traditional group A or B. McErlean et al[2] screened 1244 nasopharyngeal aspirates collected from patients aged from 1 day to 80 years who presented to Queensland hospitals or general practitioners with symptoms of acute respiratory tract infections during 2003. Among the samples screened, 17 were identified as new rhinovirus positive and the authors named the new rhinovirus as HRV-QPM, which was classified into HRV-A2. The whole genome of HRV-QPM is shorter than all other known HRVs' and isolation of the strain was unsuccessful using human cell lines HeLa-Ohio, A549, MRC-5 and W138. Kistler et al[3] used virochip to test samples from recruited adults who had cold symptoms from the fall of 2001 to December of 2004. They found 5 divergent HRVs named as HRV'X', which possessed slightly more sequence similarity to HRV-A than to HRV-B reference serotypes. None of the divergent HRV'X' isolates were culturable. Lee et al[4] used Respiratory Multicode Assay to analyze nasal lavage samples of infants. They found 5 distinct strains and proposed that they represent a new HRV genetic group (HRV-C). None of the samples containing the new HRV strains produced cytopathic effect (CPE) in standard WI-38 or MRC-5 cell cultures used for the detection and isolation of HRV. Using RT-PCR method, Lau et al[5] screened 200 Nasopharyngeal Aspirates (NPAs) collected from hospitalized children during a 1-year period (November 2004 to October 2005). They found 21 positive for HRV which belonged to a distinct genetic cluster, i.e., clade C, with nucleotide identity of <63% to known HRV-A strains and nucleotide identity of <61% to known HRV-B strains. Renwick et al[6] used MassTag PCR to investigate 97 nasopharyngeal aspirates from children hospitals during the interval of 2003-2006. They found 30 HRV sequences which did not match with known HRVA, HRVB, or Human Enterovirus (HEV) sequences.

SUMMARY OF THE INVENTION

The present invention is based on the discovery of a new Rhinovirus strain of HRV-C, named BCH019, which is believed to be associated with severe respiratory illness. The genomic sequence of BCH019 is set out in FIG. 1 and SEQ ID NO: 1. The organization of the genome of BCH019 is depicted in FIG. 2.

Accordingly, in one aspect, the present invention relates to an isolated HRV-C Rhinovirus having a RNA genome, said genome comprising a polynucleotide sequence selected from the group consisting of:
(i) a sequence identified as SEQ ID NO: 1,
ii) a sequence which exhibits at least 75% identity, preferably at least 80%, 85%, 90% or 95% identity with SEQ ID NO: 1, and
(iii) a complementary sequence of a sequence identified in (i) or (ii).

Furthermore its genome comprises at least one reading frame encoding a polyprotein, the sequence of which is identified as SEQ NO: 20.

The invention also relates to nucleic acid sequences of said virus as well as the use of the above polynucleotide or fragments thereof in designing primers or probes for detecting HRV-C Rhinovirus in a sample.

The present invention also concerns nucleic fragments comprising or consisting of at least 50 consecutive nucleotides, preferably at least 100, 150 or 200 consecutive nucleotides, belonging to a nucleotide sequence starting at nucleotide 627 and ending at nucleotide 7064 of SEQ ID NO: 1, or belonging to a nucleotide sequence which exhibits at least 85% identity, preferably at least 90 or 95% identity with the nucleotide sequence starting at nucleotide 627 and ending at nucleotide 7064 of SEQ ID NO: 1 or their complementary sequences; and especially the following fragments respectively identified in SEQ ID NO: 21 (VP4 nt 627-827 inclusive), SEQ ID NO: 22 (VP2 nt 828-1613 inclusive) and SEQ ID NO: 23 (PCR product nt 556-886 inclusive) and the variants which exhibit at least 85% identity, preferably at least 90 or 95% identity, respectively or their complementary sequences.

In another aspect, the present invention provides a pair of primers for amplifying a strain of HRV-C in a sample by PCR amplification, wherein at least one primer comprises a nucleotide sequence which consists of 18 to 30 consecutive nucleotides, especially 18 to 25 consecutive nucleotides, within the region from about nucleotide 556 to about nucleotide 886 of SEQ ID NO: 1. In a preferred embodiment, the pair of primers comprises a forward primer 556F as set out in SEQ ID NO: 6 and a reverse primer 886R as set out in SEQ ID NO: 7.

In another aspect, the present invention provides a kit for PCR amplifying a strain of HRV-C in a sample comprising at least one primer pair of the present invention as mentioned above.

In a further aspect, the present invention provides a method for detecting the presence of a strain of HRV-C in a sample, comprising the steps of:
(a) extracting nucleic acid from the sample,
(b) amplifying the extracted nucleic acid, and (c) determining the presence of one or more nucleic acid sequences, wherein the amplification step is, for instance, performed by RT-PCR, by using at least one primer pair of the present invention as mentioned above.

Other techniques exist for amplifying a target in a sample. By way of example NASBA and TMA technologies are cited.

The sample is selected from the group consisting of human oral and nasal samples (obtained from nasal lavage, nasopharyngeal aspirate, bronchial lavage, sputum, oral and nasal swabs) and viral culture supernatants.

The nucleotide sequences listed as SEQ ID Nos: 1, 21, 22 and 23 correspond to cDNA obtained from the reverse transcription of genomic RNA.

In other aspects, the invention concerns:
(a) an isolated protein:
encoded by a polynucleotide sequence selected from the group consisting of: (i) a sequence identified as SEQ ID NO: 1, (ii) a sequence which exhibits at least 75% identity with SEQ ID NO: 1, and (iii) a complementary sequence of a sequence identified in (i) or (ii); or
encoded by a nucleic fragment of a polynucleotide, the nucleotide sequence of which is defined above in (i), (ii) or (iii); or
comprising or consisting of an amino acid sequence identified as SEQ. ID. NO: 20;
(b) a polypeptide the amino acid sequence of which comprises or consists of at least 15 consecutive amino acids, preferably of at least 20 consecutive amino acids, advantageously of at least 30 consecutive amino acids of a protein as defined above in (a);
(c) an antibody having specificity against an epitope of a protein as defined above in (a) or (b);
(d) a method for detecting the presence of a strain of HRV-C in a sample comprising the steps of contacting the sample with a protein as defined above in (a) or with a polypeptide as defined above in (b) and detecting the presence of an immune complex formed between the protein or polypeptide and anti-HRV-C antibodies, for example by immuno-enzymatic methods including colorimetric, fluorescent, luminescent or electrochemistry detection such as Western Blot, sandwich immunoassay and competition technology; the sample being preferably a human sample selected from the group consisting of blood, plasma and serum;
(e) a method for detecting the presence of a strain of HRV-C in a sample comprising the steps of contacting the sample with at least one anti-HRV-C antibody having a specificity against an epitope of a HRV-C protein of the strain and detecting the presence of an immune complex of antibody/HRV-C protein, for example by immuno-enzymatic methods including colorimetric, fluorescent, luminescent or electrochemistry detection such as Western Blot, sandwich immunoassay and competition technology; the sample being preferably selected from the group consisting of human oral and nasal samples (obtained from nasal lavage, nasopharyngeal aspirate, bronchial lavage, sputum, oral and nasal swabs) and viral culture supernatants;
(f) a kit for the diagnosis of a strain of HRV-C characterized in that it comprises at least one protein or at least one polypeptide as defined above in (a) or (b);
(g) a kit for the diagnosis of a strain of HRV-C characterized in that it comprises at least one antibody as defined above in (c).

Proteins and polypeptides can be produced by recombinant technology or chemical synthesis.

Antibodies can be polyclonal antibodies, monoclonal antibodies, recombinant antibodies or fragments thereof, such as Fab, Fab', Fab'2, scFv, Fv.

These and other aspects, advantages, and features of the invention will become apparent from the following figures and detailed description of the specific embodiments.

BRIEF DESCRIPTION OF THE DRAWINGS

FIG. 1 set out the genomic sequence of BCH019.

FIG. 4 shows the PCR products obtained by using primers targeting protein coding regions of BCH019. The PCR products were separated on agarose gel.

DETAILED DESCRIPTION OF THE INVENTION

Figure 2:
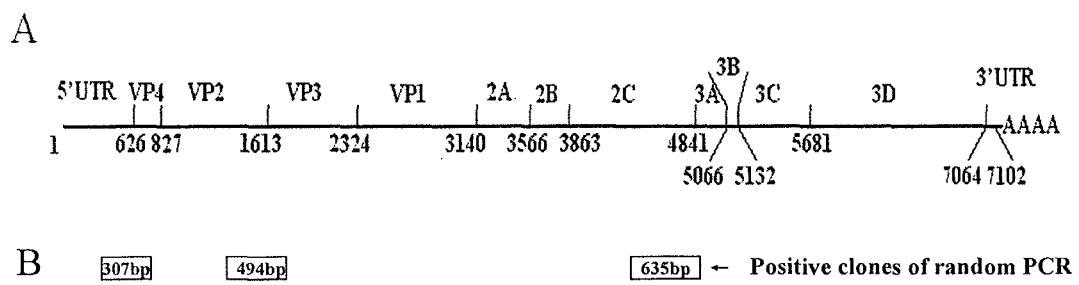
FIG. 2 depicts the genomic organization of BCH019 (panel A) and positions of the 3 different clones initially obtained by random PCR (panel B).

The present invention is based on the discovery of a new Rhinovirus strain, named BCH019, which is believed to be associated with severe respiratory illness. The full genomic sequence of BCH019 is set out in FIG. 1 and SEQ ID NO: 1. Genomic characterization showed that the full genome of BCH019 spans 7121 nt, including a 5'-UTR (626 nt), a polyprotein coding sequence (6438 nt), a 3'-UTR (38 nt), and a polyA tail (FIG. 2). The organization of the coding region of the precursor polyprotein in BCH019 is same as that in all the known HRVs, which has a highly conserved translation initiation site (encoding MGAQVS) and regions corresponding to the capsid genes VP4, VP2, VP3, VP1 and non-structural genes 2A, 2B, 2C, 3A, 3B, 3C and 3D.

Figure 3:
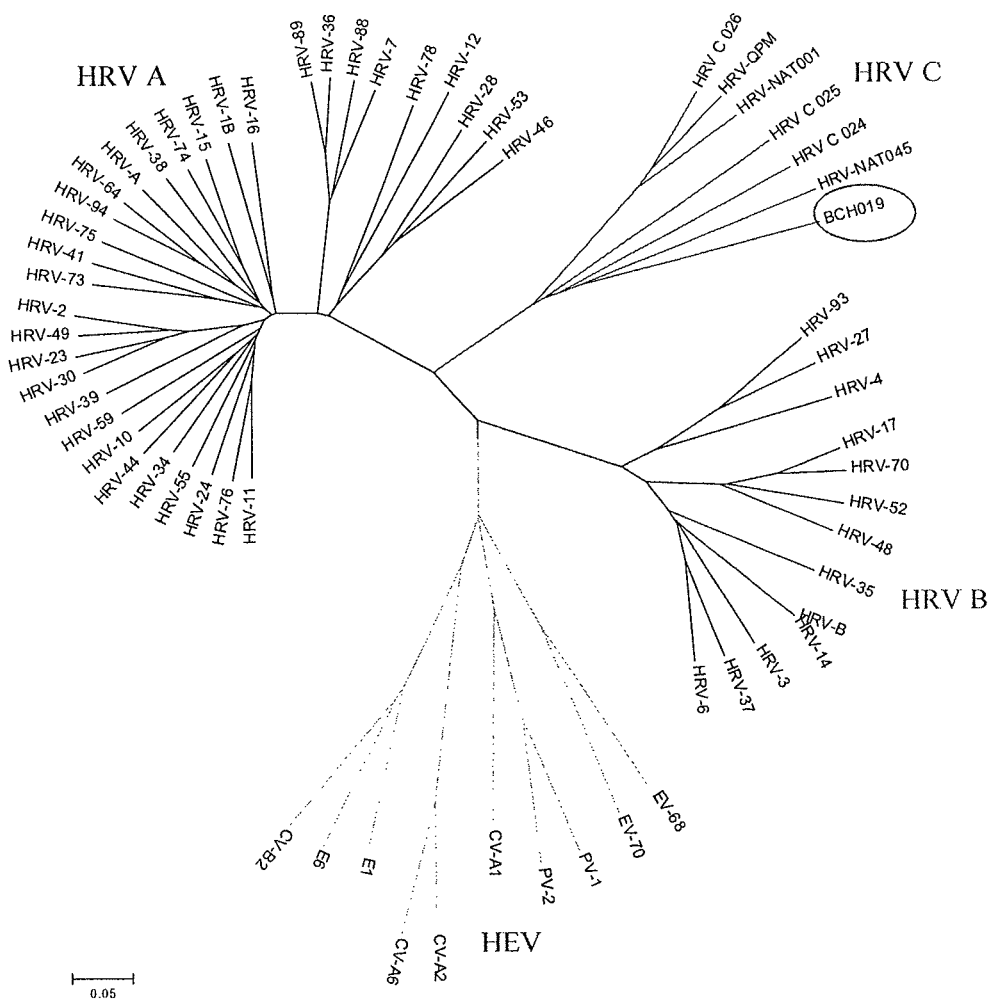
FIG. 3 shows the results of phylogenetic analysis of HRVs: bootstrapped neighbor-joining tree was constructed based on full-length nucleotide sequence of all known HRVs and some HEVs.

After phylogenetic analysis with software MEGA 4, a bootstrapped neighbor-joining tree based on full-length nucleotide sequence of all known HRVs and some HEVs was constructed and it showed that BCH019 is a distinct rhinovirus which belongs to group C of HRV rather than to group A or B (FIG. 3). VP1 is the major protein to form the canyon and the drug-binding pocket of the capsid. The canyon is the receptor-binding site. VP4 gene is the most conservative region in all the structure protein of HRVs.

The fact that BCH019 was the unique microorganism detected in the nasopharyngeal aspirate sample from a patient (sample number BCH019) clinically diagnosed as bronchopneumonia suggests a close correlation between BCH019 and the symptoms of acute lower respiratory tract infection developed in this patient.

In another aspect, the present invention provides primers, kits, and methods for specifically amplifying a strain of HRV-C in a sample by PCR amplification. The primers of the invention are designed targeting the region around the VP4 gene of BCH019. In one embodiment of the invention, at least one primer of the invention comprises a nucleotide sequence corresponding to 18-25 consecutive nucleotides within the region from about 70 bp 5'-upstream of VP4 gene to about 60 bp 3'-downstream of VP4 gene of the genomic sequence of BCH019, i.e., from about nucleotide 556 to about nucleotide 886 of SEQ ID NO: 1. In another embodiment, the region to be amplified by a primer pair of the invention includes a region about 70 bp 5'-upstream of VP4 gene (the 3'-terminal region of the 5'UTR, which is conservative for all the rhinovirus), the whole VP4 gene, and a region about 60 bp 3'-downstream of VP4 gene (the 5'-terminal region of the VP2 gene, which is conservative only for HRV-C). In this embodiment, the forward primer is designed according to the sequence of the 3'-terminal region of the 5'UTR, which is conservative for all the rhinovirus, while the reverse primer is designed according to the sequence of the 5'terminal region of the VP2 gene, which is conservative only for HRV-C.

The designing of a primer for amplifying a given nucleotide sequence is within the reach of those skilled in the art. Softwares to assist the designing of a primer are available in the art, for example, Vector NTI Advance 10 (Invitrogen). Factors to be taken into account in the designing of primers include the length, Tm, avoiding of formation of secondary structure, etc, and are also known for those in the art.

In a specific embodiment of the present invention, the forward primer is 556F (5'-ACTACTTTGGGTGTCCGT-GTTTC-3', SEQ ID NO: 6), and the reverse primer is 886R (5'-TTTCCRATAGTGATTTGCTTKAGCC-3', SEQ ID NO: 7). The region covered by this primer pair is from 70 bp 5'-upstream of VP4 gene to 59 bp 3'-downstream of VP4 gene in genome of BCH019, i.e., from nucleotide 556 to nucleotide 886 of SEQ ID NO: 1.

As shown in the examples, the primer pair of 556F and 886R was used to screen clinical samples and the results showed that some of the samples screened also contained rhinoviruses which are belong to HRV Clade C.

Accordingly, in a preferred embodiment, the present invention provides a pair of primers for amplifying a strain of HRV-C in a sample by PCR amplification, wherein the pair of primers comprises a forward primer 556F as set out in SEQ ID NO: 6 and a reverse primer 886R as set out in SEQ ID NO: 7.

The present invention further provides a kit for amplifying a strain of HRV-C in a sample comprising at least one primer pair of the present invention as mentioned above.

In a further embodiment, the present invention provides a method for detecting the presence of a strain of HRV-C in a sample from a mammal, comprising the steps of:

(a) extracting nucleic acid from the sample,
(b) amplifying the extracted nucleic acid, and
(c) determining the presence of nucleic acid sequences(s) specific for HRV-C, wherein the amplification step is, for instance, performed by an RT-PCR amplification by using at least one primer pair of the present invention.

The sample that can be tested according to the present invention can be nasal lavage, nasopharyngeal aspirate, bronchial lavage, or sputum.

With the method of the invention, it is possible to further clarify and characterize whether the infectious agent of a common cold is HRV-C and thus it would benefit the patients with a common cold by treating the patients according to the specific infectious agent.

EXAMPLES

Example 1

Identification of a New Human Rhinovirus of Group C, Named BCH019

Case Introduction

This new Rhinovirus strain was identified from nasopharyngeal aspirate sample obtained from a 2 months old male infant (sample number BCH019) clinically diagnosed as bronchopneumonia. The patient was negative for anti-IgM against CMV, EBV, HSV and CoX. An exclusion test of the nasopharyngeal aspirate sample gave negative results for known respiratory tract viruses (including human parainfluenza viruses 1-4, influenza viruses, respiratory syncytial viruse, human enteroviruses, human rhinoviruses human coronaviruses 229E, NL63, HKU1 and OC43, human metapneumovirus human adenoviruses and bocavirus). There were only normal bacteria floras in sputum culture. The nucleic acid was extracted from the nasopharyngeal aspirate sample of this patient and amplified by Random PCR in order to find unknown pathogenic microorganisms.

Random PCR

Random PCR can be used to detect both DNA and RNA viral genomes[7]. 3 different viruses have been identified using random PCR: human bocavirus[8], human KI polyomavirus[9] and human WU polyomavirus[10]. The first amplification step of Random PCR uses a first random primer with a 5' end unique nucleotide universal sequence, containing restriction enzyme sites for subsequent cloning, followed by a degenerate hexa- or heptamer sequence at the 3' end. After the first amplification step, a subsequent PCR amplification step is carried out with a second, specific primer complementary to the 5' universal region of the first random primer.

Nasopharyngeal aspirates were obtained from hospitalized children in Beijing Children Hospital in April 2007. To test the respiratory tract samples that were found negative for common pathogenic microorganisms, a random PCR method previously described[8,11] used with some modifications. In brief, the samples were centrifuged at 3000 rpm for 10 min. in a Sigma 3k30 table-top centrifuge to remove cell debris. 200 µl of the cell-free supernatant was filtered through a 0.2 µm Super® Membrane (Acrodisc® 25 mm Syringe Filter, Pall). 20 µl of RNase free DNase I (Promega) was added, and the samples were incubated for 60 min. at 37° C. Nucleic acid was extracted by using the NucliSens basic kit extraction module (bioMérieux). 10 µl of nucleic acid was mixed with 0.4 µl of universal primer FR26RV-N (5'-GCCGGAGCTCT-GCAGATATCNNNNNN-3', SEQ ID NO: 2) at 50 µM and 1.7 µl sterile deionized water. The samples were incubated at 65° C. for 5 min., and then chilled on ice. A reaction reagent mixture of 7.9 µl containing 4 µl of 5×First-Strand buffer (Invitrogen), 2 µl of 100 mM DTT (Invitrogen), 1 µl solution containing each dNTP (Invitrogen) at 10 mM, 8 units (0.4 µl) of recombinant RNase inhibitor (Ambion), and 100 units (0.5 µl) of SuperScript II reverse transcriptase (Invitrogen) was added. The reaction mixture was incubated at 25° C. for 10 min. and then 42° C. for 50 min. After a denaturation step at 94° C. for 3 min. and chilling on ice, 2.5 units (0.5 µl) of 3'-5' exo-Klenow DNA polymerase (New England Biolabs) were added, and the reaction mixture was incubated at 37° C. for 1 h, followed by an enzyme inactivation step at 75° C. for 10 min. 5 µl of each reaction mixture was used as a template in a subsequent PCR. The 50 µl reaction mixture consisted of 5 µl 10×ExTaq buffer ($Mg^{2-}$ plus) (TaKaRa), each dNTP at 0.2 mM (TaKaRa), 40 pmol of the specific primer FR20RV (5'-GCCGGAGCTCTGCAGATATC-3', SEQ ID NO: 3) (which is specific for the universal primer FR26RV-N), and 2.5 units of ExTaq (TaKaRa). After 10 min at 94° C., 40 cycles of amplification (94° C. for 1 min, 65° C. for 1 min, and 72° C. for 2 min.) were performed in GeneAmp® PCR System 9700 (Applied Biosystem).

Cloning and Sequencing PCR Products

The amplification products obtained as above were purified by using a QIAquick PCR Purification Kit (Qiagen). Products were then separated on an agarose gel and fragments between≈500 and 2000 bp in length were excised and extracted by QIAquick Gel Extraction Kit (Qiagen). Purified PCR products were ligated to the pMD18-T vector (TaKaRa) and introduced into chemically competent *E. coli* DH10B (Invitrogen). Bacteria were cultured on ampicillin-X-Gal (5-bromo-4-chloro-3-indolyl-β-D-galactopyranoside) agar plates, allowing blue-white screening. White colonies were picked and cultured for 2 h in 1 ml of Luria-Bertani broth plus ampicillin.

For subsequent PCR amplification of the cloned inserts, 1 µl of bacterial suspension was added to the PCR mixture containing 0.2 µM of the pMD18-T vector primers M13fwd (5'-CGCCAGGGTTTTCCCAGTCACGAC-3', SEQ ID NO: 4) and M13rev (5'-GAGCGGATAACAATTTCACACAGG-3', SEQ ID NO: 5), 2 mM of each dNTP, 2 µl 10×ExTaq buffer, and 1.25 U of Taq DNA polymerase in a total reaction volume of 20 µl. Cycling was performed as follows: 1 cycle of 94° C. for 3 min., followed by 30 cycles of denaturation at 94° C. for 30 s, annealing at 55° C. for 30 s, and extension at 72° C. for 1 min.

To avoid repeated sequencing of the same cloned PCR products or primer dimers, only PCR products that were larger than 250 bp and that differed in size were sent to a commercial company to get the sequence.

Obtaining the Full Genomic Sequence of BCH019

From the sample of a patient with the index sample number BCH019 who was negative for all the familiar respiratory tract viruses and bacteria tested, 185 clones of random PCR were obtained, and 6 of them were found as rhinovirus positive, representing 3 different fragments of a rhinovirus genome. Sequences of 3 initial different clones were then used to design new PCR primers to ligate the gaps step by step. 1 µl of nucleic acid extracted from BCH019 was used as template for the one-step RT PCR. The 20 µl reaction mixture consisted of 10 µl 2×Reaction Mix (Invitrogen), 1 µl Superscript™ IIIRT/Platinum® Taq Mix (Invitrogen), 20 pmol each of the primers. After 45 min at 48° C. and 3 min. at 94° C., 35 cycles of amplification were performed. Products were visualized on an agarose gel and extracted, then ligated with pMD18-T vector. After transformed into competent DH10B and cultured, the clones containing the product were sent to a commercial company to get the sequence. The terminal sequences were amplified using RACE system for rapid amplification of cDNA ends (Invitrogen).

Sequences obtained were analyzed for sequence homology with nucleotide sequences available in the GenBank database by using the BLASTn and the MEGA 4 software.

Characterization of the Genome of BCH019

The 3 initial different clones represented 3 different fragments of a rhinovirus genome (FIG. 2B). The first was 307 bp covering the region of 5'UTR/VP4, the second was 494 bp covering the region of VP2/VP3, and the third was 635 bp covering the region of 2C/3A. Series PCR primers were designed, with which most of genomic fragments were obtained step by step. Then the RACE system of Invitrogen was used to obtain the 5' end and 3' end terminal sequences of the genome. This new virus is identified as a rhinovirus and named BCH019, the entire genomic sequence of which is set out in FIG. 1 and SEQ ID NO: 1.

The genome of BCH019 spans 7121 nt, including 5'UTR (626 nt), polyprotein coding sequence (6438 nt), 3'UTR (38 nt) and polyA tail (FIG. 2A). The organization of precursor polyprotein is same as all the HRV, which has a highly conserved translation initiation site (MGAQVS) and regions corresponding to the sequences encoding structural proteins VP4, VP2, VP3, VP1 and non structural proteins 2A, 2B, 2C, 3A, 3B, 3C and 3D (FIG. 2A).

Phylogenetic Analysis

Phylogenetic tree was constructed based on alignments of BCH019 with all the complete sequence of HRV serotypes (Human rhinovirus sp. isolate NAT045 [F077280], Human rhinovirus sp. isolate NAT001 [EF077279], Human rhinovirus QPM [EF186077], Human rhinovirus C strain 026 [EF582387], Human rhinovirus C strain 025 [EF582386], Human rhinovirus C strain 024 [EF582385], HRV89 [NC 001617], B [NC 001490], 93 [EF173425], 52 [EF173424], 37 [EF173423], 3 [EF173422], 27 [EF173421], 17 [EF173420], 94 [EF173419], 78 [EF173418], 64 [EF173417], 24 [EF173416], 12 [EF173415], 11 [EF173414], 30 [DQ473512], 55 [DQ473511], 75 [DQ473510], A [DQ473509], 28 [DQ473508], 53 [DQ473507], 46 [DQ473506], 36 [DQ473505], 88 [DQ473504], 7 [DQ473503], 76 [DQ473502], 34 [DQ473501], 59 [DQ473500], 44 [DQ473499], 10 [DQ473498], 23 [DQ473497], 49 [DQ473496], 38 [DQ473495], 74 [DQ473494], 15 [DQ473493], 73 [DQ473492], 41 [DQ473491], 4 [DQ473490], 70 [DQ473489], 48 [DQ473488], 35 [DQ473487], 6 [DQ473486], 2 [X02316], 39 [AY751783], 14 [K02121], 1B [D00239], 16 [L24917]) as well as 10 HEV (Human enterovirus 68 [EF107098], Human enterovirus 70 [DQ201177], Human poliovirus type 1 [V01148], Poliovirus type 2 [X00595], Human coxsackievirus A2 [AY421760], Human coxsackievirus A6 [AY421764], Echovirus 1 [AF029859], Human echovirus 6 [AY302558], Coxsackievirus B2 [AF081485], and Human coxsackievirus A1 [AF499635]) sequences (FIG. 3).

It was found that the sequence of BCH019 represents a distinct new human rhinovirus. Even comparing with HRV NAT045, the closest HRV strain in phylogenetic tree, the similarity between BCH019 and HRV NAT045 was only 66.7%. BCH019 and some other recently discovered rhinoviruses including HRV-QPM, HRV-NAT045, 001, HRV-C 024, 025, and 026 clearly belong to a separate Glade, HRV-C.

Example 2

Verification of the Genomic Sequence of BCH019

To verify the sequence of BCH019, nucleic acid of sample BCH019 was extracted again. Newly designed specific primers targeting all the putative coding protein were used to amplify the genes. Primer VP4 (5'-ATGGGTGCACAAGT-GAGTAA-3', SEQ ID NO: 8) and primer VP2R (5'-GCTAT-TGCTTTTGGGTTTG-3', SEQ ID NO: 9) were designed to amplify VP4 and VP2 genes (FIG. 4B). Primer VP3 (5'-GGGCTACCAACCAGACTACCAA-3', SEQ ID NO: 10) and primer VP3R (5'-CGATATGTTGTTACTAGGCT-GTTC-3', SEQ ID NO: 11) were designed to amplify VP3 gene (FIG. 4D). Primer 2A (5'-GGACCCAGTGATT-TATTTGTACA-3', SEQ ID NO: 12) and primer 2BR (5'-CTGCTTGGAGGGCGGTTTA-3', SEQ ID NO: 13) were designed to amplify 2A and 2B genes (FIG. 4D). Primer 2C (5'-CAGTGGTGATGGTTGGCTC-3', SEQ ID NO: 14) and primer 2CR (5'-GCGTTGGAATATTGCATCTAG-3', SEQ ID NO: 15) were designed to amplify 2C gene (FIG. 4A). Primer 3A (5'-GATTAGGAGATTCTGAGACACCA-3', SEQ ID NO: 16) and primer 3CR (5'-CGCTGGGTGTCAT-TAAAGTATT-3', SEQ ID NO: 17) were designed to amplify 3A, 3B and 3C genes (FIG. 4D). Primer 3D (5'-TGCTATCA-CACATGTCCAAGA-3', SEQ ID NO: 18) and primer 3DR (5'-GAAATTGTCAAGCCACTGC-3', SEQ ID NO: 19) were designed to amplify 3D gene (FIG. 4C).

FIG. 4 shows the PCR products obtained by using primers targeting the protein coding regions of BCH019. At least 3 clones of each PCR products were sequenced to make sure the accuracy of the sequence of each region. The result confirmed the existence of the rhinovirus BCH019 in this sample and the accuracy of the sequence.

Example 3

Detection of HRV-Cs in Samples from Patients with Respiratory Infections

Designing PCR Primers for Determining Human Rhinovirus of Group C

VP4 gene is the most conservative region in all the structure protein, so the full-length sequences of this region of all known HRVs were compared in order to design specific primers for HRV-C. A forward primer 556F (5'-ACTACTTTGGGTGTCCGTGTTTC-3', SEQ ID NO: 6) and a reverse primer 886R (5'-TTTCCRATAGTGATTTGCTTKAGCC-3', SEQ ID NO: 7) were designed which are directed to the region from 70 bp 5'-upstream of VP4 gene to 59 bp 3'-downstream of VP4 gene of SEQ ID NO: 1. The forward primer 556F was designed according to the sequence of the 3'-terminal region of the 5'UTR, which is conservative for all the rhinovirus, while the reverse primer 886R was designed according to the sequence of the 5'-terminal region of the VP2 gene, which is conservative only for HRV-C.

To evaluate the incidence of HRV-C infection, primers 556F and 886R were used to screen clinical samples for the evidence of infection with strains of HRV-C.

Samples were extracted and amplified individually. Positive and negative controls were included in each experiment. Nucleic acid was extracted by using the NucliSens basic kit extraction module (bioMérieux). Nucleic acid (1 µl) was used as template for the PCR. The 20 µl reaction reagent mixture consisted of 10 µl 2×Reaction Mix (Invitrogen), 1 µl Superscript™ IIIRT/Platinum® Taq Mix (Invitrogen), 20 pmol each of the primers 556F (5'-ACTACTTTGGGTGTCCGTGTTTC-3', SEQ ID NO: 6) and 886R (5'-TTTCCRATAGTGATTTGCTTKAGCC-3', SEQ ID NO: 7). After 45 min. at 48° C. and 3 min at 94° C., 35 cycles of amplification (94° C. for 30 sec, 55° C. for 30 sec, and 72° C. for 1 min.) were performed. Products were visualized on an agarose gel. The expected product size was 330 bp. All PCR products were sequenced to confirm that they were specific for HRV-C.

Detection of HRV-C Infection 298 samples from BCH were screened by primers 556F and 886R and additional 13 samples were found HRV-C positive (Table 1). There were 12 males and 1 female. The age range was from 1 month 6 days to 3 years. The cases were gathered from emergency ward, pediatric ward, pediatric intensive care unit (PICU) respectively Rhinovirus is the unique respiratory virus tested in 8 cases. None cases occurred in summer (July, August and September) 2007.

Because human rhinovirus of group C is a new clade, so far it is not known if the rhinovirus of group C also has as many types as group A or B and its distribution in patients of acute respiratory tract infection. The inventors found 13 additional samples which were HRV-C positive. The result indicates that infection of the rhinovirus of group C might be common and the clinical manifestations are different as compared with infections of rhinovirus of group A or B. These data also suggest that like HRV-A and HRV-B groups, HRV-C strains are also highly genetically diverse.

TABLE 1

Clinical manifestations of 14 HRV-C positive cases.

| Sample No. | Date of hospitalization | Gender | Age | Clinical manifestations | Diagnosis | Ward | Codetection |
|---|---|---|---|---|---|---|---|
| BCH019 | April 04 | M | 1 mon 30 days | Snivel, cough | Bronchopneumonia | Pediatric ward | — |
| BCH057 | May 09 | M | 15 mon | Fever (39° C.), cough and asthma | Bronchopneumonia | Pediatric ward | — |
| BCH083 | June 19 | M | 31 mon | Snivel, cough, asthma, vomit, diarrhea, rhonchi | Bronchial asthma | Pediatric ward | — |
| BCH200 | October 15 | M | 8 mon | Cough, sputum, asthma, rhonchi and moist rale | Peribronchiolitis | Critical care room | — |
| BCH217 | October 22 | F | 5 mon | Cough, sputum, vomit, fever (40° C.), rhonchi | Pneumonia | Pediatric ward | — |
| BCH220 | October 21 | M | 17 mon | Snivel, cough, fever (38.6° C.), moist rale | Pneumonia | pediatric ward | PIV 3 |
| BCH221 | October 23 | M | 7 mon | Cough, sputum, fever (37.8° C.), moist rale | Bronchopneumonia | Pediatric ward | RSV A |
| BCH237 | October 30 | M | 1 mon 14 days | Cough, moist rale | Bronchopneumonia | PICU | — |
| BCH242 | October 31 | M | 3 yr | Cough, fever (38° C.) | Pneumonia | Pediatric ward | — |
| BCH249 | November 06 | M | 1 mon 6 days | Cough, moist rale | Bronchopneumonia | PICU | — |
| BCH250 | November 05 | M | 3 mon | Cough, sputum, moist rale | Bronchiolitis | Pediatric ward | RSV A |
| BCH264 | October 25 | M | 3 mon | Fever (38° C.) | Infant hepatitis syndrome | Ppediatric ward | RSV A |
| BCH277 | November 10 | M | 8 mon 14 days | Snivel, cough, fever (39° C.) | Pneumonia | Pediatric ward | RSV A, NL63 |
| BCH297 | November 20 | M | 50 days | Cough, sputum, rhonchi and moist rale | Pneumonia | Emergency room | RSV A |

REFERENCES

1. Papadopoulos N G and Johnston S L. Rhinoviruses. In: Zuckerman A J, Banatvala J E, Pattison J R, Griffiths P D and Schoub B D, Edited. Principles and Practice of Clinical Virology, Fifth Edition. 2004 John Wiley & Sons Ltd. Pp 361-362.
2. McErlean P, Shackelton L A, Lambert S B, Nissen M D, Sloots T P, and Mackay I M. 2007. Characterisation of a newly identified human rhinovirus, HRV-QPM, discovered in infants with bronchiolitis. J. Clin. Virol. 39:67-75.
3. Kistler A, Avila P C, Rouskin S, Wang D, Ward T, Yagi S, Schnurr D, Ganem D, DeRisi J L. and Boushey H A. 2007. Pan-viral screening of respiratory tract infections in adults with and without asthma reveals unexpected human coronavirus and human rhinovirus diversity. J Infect Dis 196: 817-25.
4. Lee W M, Kiesner C, Pappas T, Lee I, Grindle K, Jartti T, Jakiela B. 2007. A diverse group of previously unrecognized human rhinoviruses are common causes of respiratory illnesses in infants. PloS ONE 2(10):e966.
5. Lau S K P, Yip C C Y, Tsoi Hoi-wah, Lee R A, So Lok-yee, Lau Yu-lung, Chan Kwok-hung, Woo P C Y, and Yuen Kwok-yung. 2007. Clinical features and complete genome characterization of a distinct human rhinovirus (HRV)

genetic cluster, probably representing a previously undetected HRV species, HRV-C, associated with acute respiratory illness in children. J Clin Microbiol. 45(11):3655-64.
6. Renwick N, Schweiger B, Kapoor V, Liu Zhiqiang, Villari J, Bullmann R, Miething R, Briese T, and Lipkin W. I. 2007. A recently identified rhinovirus genotype is associated with severe respiratory-tract infection in children in Germany. J Infect Dis. 196:1754-60.
7. Ambrose H E and Clewley J P. Virus discovery by sequence-independent genome amplification. 2006. Rev. Med. Virol. 16: 365-83.
8. Allander T, Tammi M T, Eriksson M, Bjerkner A, Tiveljung-Lindell A, et al. 2005. Cloning of a human parvovirus by molecular screening of respiratory tract samples. Proc Natl Acad Sci USA 102: 12891-6.
9. Allander T, Andreasson K, Gupta S, Bjerkner A, Bogdanovic G, et al. 2007. Identification of a third human polyomavirus. J Virol 81: 4130-6.
10. Gaynor A M, Nissen M D, Whiley D M, Mackay I M, Lambert S B, et al. 2007. Identification of a novel polyomavirus from patients with acute respiratory tract infections. PLoS Pathog 3(5): e64.
11. Stang A, Korn K, Wildner O, and Überlal K. 2005. Characterization of virus isolates by particle-associated nucleic acid PCR. J Clin Microbiol. 43(2):716-20.

The invention claimed is:

1. An isolated human rhinovirus of genetic group C (HRV-C) comprising an RNA genome that has at least 75% sequence identity with the full-length cDNA sequence of SEQ ID NO: 1, wherein thymine nucleotides in SEQ ID NO: 1 represent uracil nucleotides in the RNA genome.

2. The isolated human rhinovirus of claim 1, wherein the RNA genome has at least 85% sequence identity with the full-length cDNA sequence of SEQ ID NO: 1.

3. The isolated human rhinovirus of claim 1, wherein the RNA genome has at least 95% sequence identity with the full-length cDNA sequence of SEQ ID NO: 1.

4. The isolated human rhinovirus of claim 1, wherein the RNA genome has the same sequence as the full-length cDNA sequence of SEQ ID NO: 1.

5. The isolated human rhinovirus of claim 1, wherein the RNA genome comprises at least one reading frame encoding a polyprotein.

6. The isolated human rhinovirus of claim 5, wherein the polyprotein has the full-length amino acid sequence of SEQ ID NO: 20.

7. An isolated DNA molecule comprising a nucleic acid sequence having at least 95% sequence identity with at least 150 consecutive nucleotides of nucleotides 627 to 7064 in SEQ ID NO: 1 or with at least 150 consecutive nucleotides of the sequence complementary to nucleotides 627 to 7064 in SEQ ID NO: 1.

8. The isolated DNA molecule of claim 7, wherein the nucleic acid sequence has at least 95% sequence identity with a full-length sequence selected from the group consisting of the full-length sequences of SEQ ID NOS: 21-23 and the sequences fully complementary thereto.

9. An isolated polypeptide produced by the rhinovirus of claim 1.

10. An isolated polypeptide encoded by the DNA of claim 7.

11. An isolated polypeptide comprising the full-length amino acid sequence of SEQ ID NO: 20.

12. A kit for diagnosing infection by a human rhinovirus of genetic group C (HRV-C) strain, the kit comprising a container containing the polypeptide of claim 10.

13. A method for detecting the presence of a human rhinovirus of genetic group C (HRV-C) strain, comprising:
   contacting a sample with the polypeptide of claim 10; and
   detecting whether an immune complex between the polypeptide and anti-HRV-C antibodies is formed,
   wherein the presence of the immune complex indicates the presence of the HRV-C strain.

14. The method of claim 13, wherein the sample is selected from the group consisting of human nasal samples, human oral samples, and culture supernatants.

* * * * *

UNITED STATES PATENT AND TRADEMARK OFFICE
CERTIFICATE OF CORRECTION

PATENT NO.       : 8,709,779 B2
APPLICATION NO. : 12/936004
DATED            : April 29, 2014
INVENTOR(S)      : Gonzalez et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 373 days.

Signed and Sealed this

Twenty-ninth Day of September, 2015

Michelle K. Lee
*Director of the United States Patent and Trademark Office*